US012521287B2

(12) United States Patent
Rössler et al.

(10) Patent No.: US 12,521,287 B2
(45) Date of Patent: Jan. 13, 2026

(54) ABSORBENT FIBROUS WEB

(71) Applicant: Essity Hygiene and Health Aktiebolag, Gothenburg (SE)

(72) Inventors: Joraine Rössler, Gothenburg (SE); Anna Nihlstrand, Gothenburg (SE); Lars Fingal, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 184 days.

(21) Appl. No.: 17/783,293

(22) PCT Filed: Dec. 2, 2020

(86) PCT No.: PCT/SE2020/051158
§ 371 (c)(1),
(2) Date: Jun. 8, 2022

(87) PCT Pub. No.: WO2021/126042
PCT Pub. Date: Jun. 24, 2021

(65) Prior Publication Data

US 2023/0028309 A1 Jan. 26, 2023

(30) Foreign Application Priority Data

Dec. 20, 2019 (SE) .................................... 1951524-6

(51) Int. Cl.
*A61F 13/53* (2006.01)
*A61F 13/15* (2006.01)
(Continued)

(52) U.S. Cl.
CPC ........... *A61F 13/53* (2013.01); *D04H 1/4258* (2013.01); *D04H 1/492* (2013.01);
(Continued)

(58) Field of Classification Search
CPC .................... A61F 13/53; A61F 13/531; A61F 2013/15983; A61F 2013/530036;
(Continued)

(56) References Cited

U.S. PATENT DOCUMENTS

| | | | | |
|---|---|---|---|---|
| 5,486,167 A | | 1/1996 | Dragoo et al. | |
| 5,853,538 A | * | 12/1998 | Reiner | D21F 11/002 162/190 |

(Continued)

FOREIGN PATENT DOCUMENTS

| | | |
|---|---|---|
| CN | 1126067 A | 7/1996 |
| CN | 1137585 A | 12/1996 |

(Continued)

OTHER PUBLICATIONS

Kaplan, Sibel, Sebile Pulan, and Seyhan Ulusoy. "Objective and subjective performance evaluations of wet wipes including herbal components." Journal of Industrial Textiles 47.8 (2018): 1959-1978. (Year: 2018).*

(Continued)

*Primary Examiner* — Michael Zhang
(74) *Attorney, Agent, or Firm* — BUCHANAN INGERSOLL & ROONEY PC

(57) ABSTRACT

The present disclosure relates to an absorbent fibrous web, in which the fibres are constituted by cellulosic fibres including cellulosic staple fibres and cellulose pulp fibres and the absorbent fibrous web is a foam-formed hydro-entangled fibrous web. The present disclosure further relates to a method of manufacturing such an absorbent fibrous web.

21 Claims, 4 Drawing Sheets

(51) Int. Cl.
*D04H 1/4258* (2012.01)
*D04H 1/492* (2012.01)

(52) U.S. Cl.
CPC ............... *A61F 2013/15983* (2013.01); *A61F 2013/530036* (2013.01); *D10B 2509/026* (2013.01)

(58) Field of Classification Search
CPC ...... A61F 2013/530058; D04H 1/4258; D04H 1/492; D04H 1/43835; D04H 1/465; D04H 1/65; D10B 2509/026; A61K 8/0208
See application file for complete search history.

(56) References Cited

U.S. PATENT DOCUMENTS

| | | | |
|---|---|---|---|
| 6,017,833 A | 1/2000 | Reiner et al. | |
| 6,110,848 A * | 8/2000 | Bouchette | D04H 1/732 442/389 |
| 9,161,865 B2 | 10/2015 | Paveletzke et al. | |
| 11,602,466 B2 * | 3/2023 | Bagger-Sjöbäck | D04H 1/4258 |
| 11,801,173 B2 * | 10/2023 | Bagger-Sjöbäck | A61L 15/28 |
| 2002/0088099 A1 | 7/2002 | Ahoniemi | |
| 2003/0213108 A1 | 11/2003 | Strandqvist | |
| 2005/0022954 A1 * | 2/2005 | Strandqvist | D21H 27/02 162/100 |
| 2005/0155199 A1 | 7/2005 | Stralin et al. | |
| 2007/0178795 A1 * | 8/2007 | Stralin | D04H 1/43835 442/361 |
| 2010/0274208 A1 | 10/2010 | Gabrielii et al. | |
| 2012/0244320 A1 * | 9/2012 | Sauter | D21H 27/002 264/293 |
| 2013/0313149 A1 | 11/2013 | Hird et al. | |
| 2014/0170402 A1 | 6/2014 | Knowlson et al. | |
| 2015/0083354 A1 | 3/2015 | Strandqvist | |
| 2017/0203542 A1 | 7/2017 | Ramaratnam et al. | |
| 2018/0355527 A1 | 12/2018 | Strandqvist et al. | |
| 2018/0363177 A1 | 12/2018 | Strandqvist | |
| 2019/0276958 A1 | 9/2019 | Konishi | |
| 2020/0040528 A1 * | 2/2020 | Pihko | D21F 1/028 |
| 2021/0222335 A1 * | 7/2021 | Maier | D04H 1/492 |
| 2023/0042528 A1 | 2/2023 | Bagger-Sjöbäck et al. | |

FOREIGN PATENT DOCUMENTS

| | | | | |
|---|---|---|---|---|
| CN | 1948613 | A | 4/2007 | |
| CN | 100558980 | C | 11/2009 | |
| CN | 103118646 | A | 5/2013 | |
| CN | 11191692 | A | 8/2019 | |
| EP | 3382078 | A1 | 10/2018 | |
| JP | H1193055 | A | 4/1999 | |
| WO | 9602701 | A1 | 2/1996 | |
| WO | 03069038 | A1 | 8/2003 | |
| WO | 03083197 | A1 | 10/2003 | |
| WO | 2005002842 | A1 | 1/2005 | |
| WO | 2005007962 | A1 | 1/2005 | |
| WO | 2005042819 | A2 | 5/2005 | |
| WO | 2006001739 | A1 | 1/2006 | |
| WO | 2010021572 | A1 | 2/2010 | |
| WO | 2012090130 | A2 | 7/2012 | |
| WO | 2012150902 | A1 | 11/2012 | |
| WO | WO-2013136471 | A1 * | 9/2013 | D21H 27/002 |
| WO | 2017079169 | A1 | 5/2017 | |
| WO | 2018065668 | A1 | 4/2018 | |
| WO | 2019239012 | A1 | 12/2019 | |

OTHER PUBLICATIONS ip.com Translation of WO-2013136471-A1 (Year: 2024).*

International Preliminary Report on Patentability (PCT/IPEA/409) mailed on Mar. 2, 2022 for International Application No. PCT/SE2019/051330. (7 pages).

International Preliminary Report on Patentability (PCT/IPEA/409) mailed on Mar. 2, 2022 for International Application No. PCT/SE2019/051331. (8 pages).

International Search Report (PCT/ISA/210) and Written Opinion (PCT/ISA/237) mailed on Sep. 2, 2020, by the Swedish Patent Office as the International Searching Authority for International Application No. PCT/SE2019/051330. (16 pages).

International Search Report (PCT/ISA/210) and Written Opinion (PCT/ISA/237) mailed on Sep. 2, 2020, by the Swedish Patent Office as the International Searching Authority for International Application No. PCT/SE2019/051331. (15 pages).

Written Opinion of the International Preliminary Examining Authority (PCT/IPEA/408) mailed on Dec. 1, 2021 by the European Patent Office as the International Searching Authority for International Application No. PCT/SE2019/051330. (5 pages).

Written Opinion of the International Preliminary Examining Authority (PCT/IPEA/408) mailed on Dec. 1, 2021 by the Swedish Patent Office as the International Searching Authority for International Application No. PCT/SE2019/051331. (7 pages).

Corrected International Search Report (PCT/ISA/210), Corrected Written Opinion (PCT/ISA/237), Communication in Cases for Which No Other Form is Applicable (PCT/ISA/224) mailed on Feb. 1, 2021 by the Swedish Patent Office as the International Searching Authority for International Application No. PCT/SE2020/051158. (12 pages).

Notification of the First Office Action issued on Jan. 20, 2023, by the Chinese Patent Office in corresponding Chinese Patent Application No. 202080083295.7, and an English Translation of the Office Action. (15 pages).

Office Action issued on Jun. 8, 2023, in corresponding Chinese Patent Application No. 202080083295.7 and English translation of the Office Action. (15 pages).

Office Action issued on Mar. 13, 2023, by the U.S. Patent and Trademark Office in U.S. Appl. No. 17/783,332.

Office Action issued in Chinese Patent Application No. 201980102567.0, dated Nov. 4, 2022, with English Translation (24 pages).

Notice of Allowance issued in U.S. Appl. No. 17/783,335, dated Jan. 26, 2023 (17 pages).

Decision of Rejection issued in Chinese Patent Application No. 2019801025543 dated Mar. 2, 2023, with English Translation (12 pages).

Office Action issued on Sep. 5, 2023, in corresponding Chinese Patent Application No. 202080083295.7 and English translation of the Office Action. (13 pages).

Supplementary European Search Report issued on Jan. 8, 2024, by the European Patent Office in corresponding European Patent Application No. 20902302.7 (6 pages).

* cited by examiner

ABSORBENT FIBROUS WEB

TECHNICAL FIELD

The present disclosure relates to an absorbent fibrous web and to a method of manufacturing such an absorbent fibrous web.

BACKGROUND

Absorbent fibrous webs may be used to make hygiene and wiping products. The hygiene and wiping products are typically made by cutting the absorbent fibrous web into sheets or rolling the absorbent fibrous web to rolls of a suitable size for an end user. Sometimes, two or more absorbent fibrous webs are combined into a single product, the absorbent fibrous webs thereby forming plies of the combined product. The plies may thereby be connected to each other by means of embossing and/or an adhesive. In addition, one or more absorbent fibrous webs may be used as one or more layers in a hygienic absorbent article intended for absorption of a body fluid, such as a panty-liner, sanitary towel, incontinence article or a diaper.

Typical properties of these hygiene and wiping products include their ability to absorb tensile stress energy, their drapability, good textile-like flexibility, properties which are frequently referred to as bulk softness, a high surface softness and a high specific volume with a perceptible thickness. A liquid absorbency, often as high as possible, and, depending on the application, a suitable wet and dry strength as well as an appealable visual appearance of the outer product's surfaces are desired. These properties, among others, allow these hygiene and wiping products to be used, for example, as cleaning wipes, industrial wipes, household towel or the like; as sanitary products such as for example bathroom tissue, handkerchiefs, household towels, towels and the like; as cosmetic wipes, such as for example facials and as serviettes or napkins, just to mention some of the products that may be used. Furthermore, the hygiene and wiping products may be dry, moist, wet, printed or pretreated in any manner. In addition, the hygiene and wiping products may be folded, interleaved or individually placed, stacked or rolled, connected or not, in any suitable manner.

Some of these desired properties may sometimes be contradictory. Purely as an example, increasing the strength may result in a decreased softness of the product and vice versa. There is thus a desire to provide an absorbent fibrous web making it possible to obtain a suitable level of the desired properties of the product without sacrificing other properties.

In some of the hygiene and wiping products existing on the market, the desired properties are obtained by utilizing manmade materials, such as fossil-based materials. However, there is a general desire to be able to provide hygiene and wiping products being made of renewable raw materials only.

Even if there exist many hygiene and wiping products based on renewable raw materials, such as products made of tissue paper, there may e.g. be a desire to make them more textile-like.

Accordingly, there is a desire to overcome or ameliorate at least one of the disadvantages of the prior art, or to provide a useful alternative.

SUMMARY

One or more of the above objects may be achieved with an absorbent fibrous web in accordance with claim 1. Further embodiments are set out in the dependent claims and in the following description.

Herein it is disclosed an absorbent fibrous web, the fibres of the absorbent fibrous web being constituted by cellulosic fibres comprising cellulosic staple fibres and cellulose pulp fibres. The absorbent fibrous web is a foam-formed hydroentangled fibrous web.

The absorbent fibrous web may be used to manufacture wiping material, e.g. as a hand wiping material, a hygiene tissue and/or as a layer in an absorbent article for absorption of a body fluid. Thereby the absorbent fibrous web may be cut into sheets, rolled to rolls of a suitable size for an end user or shaped as the absorbent article.

The term "cellulosic staple fibres" as used herein comprises man-made and/or natural cellulosic fibres. Examples of man-made cellulosic fibres, also called regenerated cellulosic fibres, are lyocell or viscose. Examples of natural cellulosic fibres are seed hair fibres, e.g. cotton, kapok, and milkweed; leaf fibres, e.g. sisal, abaca, pineapple, and New Zealand hemp; or bast fibres e g flax, hemp, jute and kenaf.

If the cellulosic staple fibres are man-made fibres, they may be treated with spin finish and crimped, but this is not necessary for the type of processes preferably used to produce the material described in the present disclosure. Spin finish and crimp is normally added to ease the handling of the fibres in a dry process, e.g. a card, and/or to give desired properties, e.g. hydrophilicity, to a material consisting only of these fibres, e.g. a nonwoven top sheet for a diaper. However, the method herein instead comprises foam-forming, which is further described below.

The cutting of the fibre bundle to staple fibres is normally done to result in a single cut length, which may be altered by varying the distances between the knives of the cutting wheel. Thereby the fibre length may be set depending on the planned use of the staple fibres.

The term "cellulosic staple fibres" as used herein comprises both fibres, which have been cut from fibre bundles to a length being within a desired length range, and fibres having a natural length being within the desired length range, e.g. some of the natural cellulosic fibres mentioned above, also called staple-length fibres. The desired length may e.g. be in the range of 2-25 mm, such as within the range of 2-20 mm, 5-15 mm or 6-12 mm.

The term "cellulose pulp fibres" as used herein comprises pulp fibres from chemical pulp, e.g. kraft, sulphate or sulphite, mechanical pulp, thermo-mechanical pulp, chemo-mechanical pulp and/or chemo-thermo-mechanical pulp, abbreviated as CTMP. Pulps derived from both deciduous (hardwood) and coniferous (softwood) may be used. Fibres may also come from non-wood plants, e.g. cereal straws, bamboo, jute or sisal. The fibres or a portion of the fibres may be recycled fibres, which may belong to any or all of the above categories.

Additives such as softeners, as quaternary ammonium compounds, dry-strength agents or wet-strength agents may be added in order to facilitate manufacturing of the absorbent fibrous web or to adjust the properties thereof. However, for some embodiments of the absorbent fibrous web, the absorbent fibrous web may be so strong in itself, that there is no need for a dry strength agent or and/or a wet strength agent to improve strength.

The absorbent fibrous webs as used herein are foam-formed webs. Foam-forming is a type of wetforming which involves dispersing the fibres in a foamed liquid containing water and a surfactant. Foam-forming creates bulky high porosity webs.

Patent document WO 9602701 A1 describes a method of producing a nonwoven material involving hydroentangling of a fibre web, whereby dry fibres, natural and/or synthetic, are metered into a dispersion vessel, possibly after pre-wetting, the fibres being dispersed in a foamable liquid comprising water and a surfactant, for forming a foamed fibre dispersion, which is applied to a fabric and drained. The formed fibre web is subjected to hydroentangling directly after forming and the foamable liquid, after having passed through the fabric, is recirculated to the dispersion vessel in a simple closed circuit.

The absorbent fibrous web as disclosed herein may have a large proportion of the fibres oriented at an angle to the plane of the web such that the fibres extend at least partly in the Z-direction of the web. As used herein, the Z-direction of the web is perpendicular to the X-direction and the Y-direction, which define the planar extension of the web. The Z-direction is also referred to herein as the thickness direction of the web. The Z-directionality of the fibres may be influenced by the web being hydro-entangled. Hydro-entangling involves exposing the formed web to high-pressure water jets which move fibres out of the plane of the web. Hydroentangling may be performed on one side of the web or on both sides.

The Z-directionality of the fibres in the web may also be enhanced during wetforming of the web by dewatering the web from both sides, e.g. as disclosed in WO 2018/065668 A1. Depending on the forming fabrics used and the dewatering speed, the webs formed according to the method in WO 2018/065668 A1 may be provided with a high degree of likesidedness, which may be advantageous in some applications.

Since all the fibres used in the absorbent fibrous web are of cellulosic origin, the absorbent fibrous web as disclosed herein is made of renewable raw materials.

Further, the absorbent fibrous web as disclosed has a textile-like character, which is appreciated in many user situations, e.g. for handwiping. Products, such as hand wipes, made of the absorbent fibrous web may be both strong enough and soft at the same time, which contributes to a high user experience both when handling them dry and for wiping purposes. The textile-like character may be felt both in a dry and a wet state.

The cellulosic staple fibres and the cellulose pulp fibres may be mixed with each other. Hence there may be a mixture of cellulosic staple fibres and cellulose pulp fibres throughout the whole extension of the absorbent fibrous web as seen in the Z-direction.

The cellulosic fibres located in a first surface layer may have a similar fibre composition and/or a similar orientation of fibres as the cellulosic fibres located at a second surface layer being opposite to the first surface layer. This makes it possible to provide a web being symmetric in the Z-dimension, i.e. having two similar surfaces and thus avoiding two-sidedness. The surface layer may be defined as the x % of the thickness, i.e. in the Z-dimension, being closest to the respective surface of the absorbent fibrous web, wherein x % may be in the range of 2-20%, such as 5-15%, e.g. 10%.

The cellulosic staple fibres may have a length in the range of 2-25 mm, such as in the range of 2-20 mm, 5-15 mm or 6-12 mm. The cellulosic staple fibres may all have the same or substantially the same length or a plurality of different lengths may be used.

The cellulosic staple fibres may have a linear density within the range of 0.3-3 dtex, such as 0.5-2.4 dtex or 0.8-2.0 dtex. Dtex is a unit for linear density of fibres and yarns and gives the weight in grams of 10 km of the fibre or yarn.

The cellulosic staple fibres may make up in the range of 2-50% of a total weight of the cellulosic fibres, such as in the range of 2-40%, 5-25% or 10-17%.

The cellulose pulp fibres make up in the range of 50-98% of a total weight of the cellulosic fibres, such as in the range of 60-98%, 75-95% or 83-90%.

The absorbent fibrous web may have a basis weight, also called grammage herein, in the range of 10-250 gsm, such as in the range of 10-200 gsm, 12-190 gsm, 14-160 gsm or 15-150 gsm, with gsm being grams per square metre, $g/m^2$. If used for handwiping, the absorbent fibrous web may have a grammage within the range of 20-80 gsm, such as from 25-60 gsm, or 30-50 gsm.

The absorbent fibrous web may be micro-embossed. One or both of the surfaces may be micro-embossed, i.e. the surface being in contact with an embossing roller. The term "micro-embossing" is used herein for embossing with an embossment pattern with a dense configuration. Typically, the pattern may comprise dots or knobs in the range of from 25 to 100 dots per $cm^2$, e.g. 35 to 90 or 40 to 80 dots per $cm^2$. The micro-embossing may be seen as a surface treatment. It may help to improve the softness of the hygiene and wiping product.

The absorbent fibrous web may have a TS7 Softness value of less than 25, such as less than 20 or less than 18 as measured with the TSA method described herein. Lower TS7 value means softer material, which contributes to giving the user of the tested material a more textile-like feeling. It is thus desirable to have as low value as possible. As mentioned in the method description, the TSA method has demonstrated to correlate well with hand panel tests for thin materials like tissue or nonwoven.

The absorbent fibrous web may have a TS750 Roughness value of less than 40, such as less than 30, less than 25, or less than 20 as measured with the TSA method described herein. Higher TS750 values correspond to higher roughness and lower values thus means softer material. It is thus desirable to have as low value as possible, which contributes to giving the user of the tested material a more textile-like feeling. As mentioned in the method description, the TSA method has demonstrated to correlate well with hand panel tests for thin materials like tissue or nonwoven.

The absorbent fibrous web may have a Wetting Time, as measured with the MMT method described herein, taken as an average for both surfaces of the absorbent fibrous web and as an average of top and bottom, of less than 2.3 s, such as less than 2.2 s, less than 2.1 s, or less than 2.0 s.

The absorbent fibrous web may have a Spreading Speed, as measured with the MMT method described herein, taken as an average for both surfaces of the absorbent fibrous web and as an average of top and bottom, of over 6 mm/s, such as in the range of 6-18 mm/s, 8-16 mm/s or 10-15 mm/s.

The absorbent fibrous web may have an Absorption Time of less than 1.0 s, such as less than 0.9 s, as measured with the AWR method described herein.

The absorbent fibrous web may have a Water Spreading Length in a machine direction, MD, of the absorbent fibrous web of at least 60 mm, such as at least 70 mm or at least 80 mm, as measured with the AWR method described herein.

The absorbent fibrous web may have an Air Permeability of at least 800 mm/s, such as at least 1000 mm/s, at least 1500 mm/s or at least 1800 mm/s as measured with the method described herein.

Disclosed herein is further a use of the absorbent fibrous web as described herein as a wiping material, e.g. as a hand wiping material, a hygiene tissue and/or as a layer in an absorbent article for absorption of a body fluid.

Further, it is disclosed herein a method of manufacturing an absorbent fibrous web as described herein. The method comprises the steps of:

foam-forming a mixture of cellulosic fibres, the cellulosic fibres comprising cellulosic staple fibres and cellulose pulp fibres, two-sided dewatering of the mixture to form an intermediate web, wherein the method further comprises the step of hydro-entangling the intermediate web.

The process of foam-forming and the cellulosic fibres are described above.

Two-sided dewatering may be performed with a gap-former, e.g. the apparatus and the method described in WO 2018/065668 A1. A gap former utilizes two forming fabrics, which form a gap into which the furnish is fed. The furnish may be a mixture of foam and fibres, see examples described in WO 2018/065668 A1. The headbox may be multilayered, e.g. having 2-5 layers, such as e.g. 3 or 5 layers. With a gap-former, such as the apparatus and the method described in WO 2018/065668 A1, it is possible to obtain a material with a high degree of likesidedness.

After foam-forming and dewatering, the intermediate web is subjected to at least one hydroentangling step. Hydroentangling may be performed on one side of the intermediate web or on both sides. The hydroentangling may be performed in line with foam-forming and dewatering or in a separate unit. In the first case, one of the forming fabrics may be used during hydroentangling as well. There may also be an intermediate press-section, in between the forming section and the hydroentangling section, such that the intermediate web is subjected to pressing before it is hydroentangled.

The step of hydroentangling has a huge effect on many of the properties characterizing the absorbent fibrous web. For example, at least part of the fibres will be re-oriented during hydro-entangling, which will influence properties such as air permeability and spreading of liquids in the material.

The method may further comprise micro-embossing on at least one surface of the absorbent fibrous web. This is normally done on a dry web.

Methods

Determining Basis Weight and Density of a Web Sample

The sample is weighed to the third decimal. The area of the sample is then determined, and basis weight is obtained by dividing the sample weight by the sample area. Basis weight is reported in the unit g/m$^2$ (gsm).

Web thickness is measured under a pressure of 0.5 kPa. A suitable thickness gauge should have an accuracy of 0.01 mm. Pressure is exerted from a square foot measuring 50×50 mm. The foot is gently lowered onto the sample, and a thickness value is read after 5 seconds.

Bulk is obtained by dividing the sample volume by the sample weight and should be reported in the unit cm$^3$/g. Density is obtained by dividing the sample weight by the sample volume and should be reported in the unit kg/m$^3$.

A mean value is reported from measurements of 6-10 representative samples.

Softness Test Method—TSA Method

Softness, smoothness and stiffness properties of different sheet materials may be analysed with a softness test method by means of a TSA instrument, TSA being an abbreviation for Tissue Softness Analyzer. The method uses acoustic waves and has demonstrated to correlate well with hand panel tests for thin materials like tissue or nonwoven. The softness test method may therefore be used for determining suitable softness, smoothness and stiffness of a tissue or nonwoven material.

The test method follows the general outline of the TSA instrument manual dated 2013 Jul. 8 (Leaflet collection of the TSA Operating Instruction, Multi Functional Measuring System, Tissue Softness Analyzer, 2018 Oct. 5, available from Emtec Electronic GmbH (Gorkistrasse 31; D-04347 Leipzig, Germany) with the settings or modifications as set forth therein or below.

Technical Basics of TSA

The hand feel of a fibrous material is affected by components at various levels; from the polymers at a molecular level to the fibrous network at a macro level. Stiffness of individual fibres, internal structure, fibre-to-fibre bond strength, softener chemicals, etc. all affect the hand feel, but so do any mechanical treatment to which the web material is subjected, such as creping, and embossing. The TSA analysis may measure the effects of material differences at various levels.

Measuring Principle

The sample will be fixed in a measuring cell like a drumhead. Below is placed a vibration sensor, above is placed a vertical movable measuring head with a rotating blade that is pushed onto the sample with a defined load. In step 1 of the procedure, a rotation with defined speed is executed. The motion of the blades over the sample generates different types of vibrations/noise, which is detected with a vibration sensor. In step 2 of the procedure, the sample is deformed perpendicular to the surface to measure elastic, viscoelastic and plastic properties.

Evaluation

The resulting vibrations/noise spectrum from step 1 of the measurement is an overlapping of two single spectra; (a) Vertical vibration of the sample like a membrane and (b) Excitation of horizontal vibrations of the blades itself caused by momentary blocking and swinging back of the blades by the fibres when moving over the surface.

In step 2 of the measurement the rotor applies a defined load in three cycles in a vertical direction onto the sample, the load (F) being 0 mN, 100 mN and constant of 600 mN. Reference is made to the EMTEC manual for further details of the measuring principle. The measured D—stiffness correlates with the stiffness of the material. A low D value corresponds to a stiffer material at the same time as a higher value corresponds to a more flexible and textile-like material.

Thus, the method results in three parameters, namely TS7—softness, TS750—roughness and D—stiffness, as defined in TSA Operating Instructions 2018 Oct. 5 (Multi Functional Measuring System, Tissue Softness Analyzer). The parameters are all of relevance for evaluating whether an article may possess a soft and/or cloth-like feeling to a wearer. A high value of D and low values of TS7 and TS750 have shown to correspond to the provision of a desired soft material as touched upon by a human hand. Lower TS7 value means softer material. Higher TS750 values correspond to higher roughness and lower values consequently means softer material.

Apparatus, Materials and Conditions

As mentioned above, the test follows the general outline of the TSA instrument manual dated 2018 Oct. 5 (Multi Functional Measuring System, Tissue Softness Analyzer) that is available from Emtec Electronic GmbH with the settings or modifications as set forth therein or herein.

A Tissue Soft Analyzer (TSA) from Emtec Electronic GmbH (TSA Tissue Softness Analyzer, model B458; UC version 1.86, Series no.: 16-02-02-04-27; Software: emtec 3.29; Hard Ware: 2.0a and Windows 7 Enterprise Service pack 1) was used in the measurements according to the method.

The Sample diameter was 112.8 mm, the tested diameter was about 70 mm, and the standard rotor (about 59 mm in diameter) of the instrument was used at a rotation speed of 2 rps.

The Softness resonance frequency peak of the measurements was 6,500 Hz.

All measurements and calibrations were performed at standard climatic conditions of 23° C. (±1° C.) and 50% r.H. (±5%) in general following ISO DIN EN 20187.

The principle for TSA measurement is outlined in TSA Operating Instruction No. 12, Collection of the TSA Operating Instruction, Multi Functional Measuring System, Tissue Softness Analyzer, 2018 Oct. 5, available from Emtec Electronic GmbH.

During the measurements referred to herein, 6-10 measurements were made for each sample, 3-5 from each side.

MMT

MMT stands for Moisture Management Tester. Conditioning and testing climate were made and set according to SS-EN ISO 139:2005, i.e. (20+/−2) degree C. and 65+/−4 relative humidity, a climate which is typical for textile testing. Liquid Moisture Management Properties were determined according to AATCC Test Method 195-2011. The liquid was dosed from the top sensor. Five specimens 8×8 cm were measured for each sample, specimens 1-3 with a first side upwards from where the liquid was dosed and specimens 4-5 with the other side upwards.

Testing Equipment: SDL Atlas MMT (Moisture Management Tester) with software 3.06. Conductivity of sodium chloride solution during measurement: 16±0.2 mS.

Pump time: 20 sec

Measuring Time: 120 sec

AWR

AWR is a method developed in order to measure:

Absorption time

Water Spreading Length MD

Water Spreading Length CD

Rewet

In the measurements referred to herein, 4 measurements were made for each sample.

Equipment:

Testing condition: 23 C+/−1 and 50%+/−2 Relative humidity (rh)

Testing liquid: deionized water with 1 drop of nykockin (red pigment).

Filter paper: 90×120 mm, 440 g/m$^2$ per sheet, Quality 167 from Munktell Ahlstrom.

A smooth, liquid impermeable polyethylene film (type not critical, used to fasten the sample on and to avoid liquid on lab bench).

Stop watch, accuracy+/−0.1 s

Timer, accuracy+/−0.5 s

Metallic Ruler

Laboratory balance with 2 decimals, accuracy+/−0.03 g

Automatic pipette, Eppendorf Research 5000 (0.5 ml)

Camera

Sample Preparation:

Punch out samples to a size of 50 mm×100 mm, wherein the 100 mm length coincides with the machine direction, MD, of the sample. Condition the samples at 23 C and 50% rh for minimum 4 hours. Cut a piece of the polyethylene film to a size larger than the sample. Place the sample on the polyethylene film and fasten/secure the sample to the polyethylene film by tape at the edges. For determination of the absorption time, spreading length and rewet, the sample should rest flat on a laboratory bench.

Procedure—Absorption Time and Spreading Length:

Manually dose 0.5 ml of the testing liquid using the automatic pipette, 10 mm distance to the sample surface, to the centre of the sample, i.e. the point where the longitudinal centreline crosses the transverse centreline. Start the stop watch and the dosing simultaneously. Stop the stop watch when all liquid is absorbed into the sample, i.e. when there is no more free fluid on the sample surface. Note the absorption time.

Place the ruler along the longitudinal (MD) and transverse (CD) centrelines of the sample 5 seconds after the liquid dose has been absorbed, and determine the spreading length, i.e. the extension of the wet area in the fibrous web. Take a photo of the sample.

Procedure—Rewet

Rewet is measured 1 minute after the liquid dose has been absorbed. A stack of five pre-weighed filter papers is centred on top of the sample, with rough side of the filter papers facing the sample. A 5.5 kg weight with bottom dimension 90×120 mm, i.e. exerting a pressure of 5 kPa, is gently lowered on top of the stack. After 15 seconds the weight is removed, the filter papers are weighed, and liquid rewet is determined. Take a photo of the sample after the rewet.

Air Permeability

Equipment: TEXTEST Instruments, FX 3300, LabAir, Mark 4, TEXTEST AG Zurich Switzerland Standard Method: EDANA NWSP 070.1.R0 (15) Air Permeability of Nonwoven Materials.

Differential pressure 200 Pa and 20 cm$^2$.

Data presented in unit mm/s, also called l/m$^2$/s.

Panel Test

The panel test involved. 36 persons. Samples were tested in a dry state and as used for hand wiping.

Handled Dry:

The test was performed as blind tests. Panellist's vision was obscured by curtain hanging over their hands to avoid visual rating. They were handed one towel at a time in random order and the towel was presented folded, typical M-folded hand towel.

Question was the following:

"Take one (1) towel and rate the overall perception of the towel when handled dry on a scale from 1 to 7, where 1=Very bad and 7=Very good.

Consider both folded and unfolded.

Do not rate on visual impression."

Handwiping Experience:

Thereafter, the persons were asked to wash and wipe their hands, i.e. using the sample as a hand towel. Two towels were placed besides a wash bassinet with liquid soap. The order in which the products were tested was randomized.

Question was the following:

"Wash your hands with soap and take one towel after another (max two (2) towels) to dry your hands.

Rate the overall impression of hand wiping experience—during and after wiping—on a scale from 1 to 7, where 1=very bad and 7=very good.

Do not rate on visual impression."

BRIEF DESCRIPTION OF THE FIGURES

The absorbent fibrous web as disclosed herein will hereinafter be further explained by means of non-limiting examples with reference to the appended figures wherein.

DETAILED DESCRIPTION

In order to compare products made with the absorbent fibrous web as described herein comparisons were made between different materials suitable for handwiping.

Figure 1A:
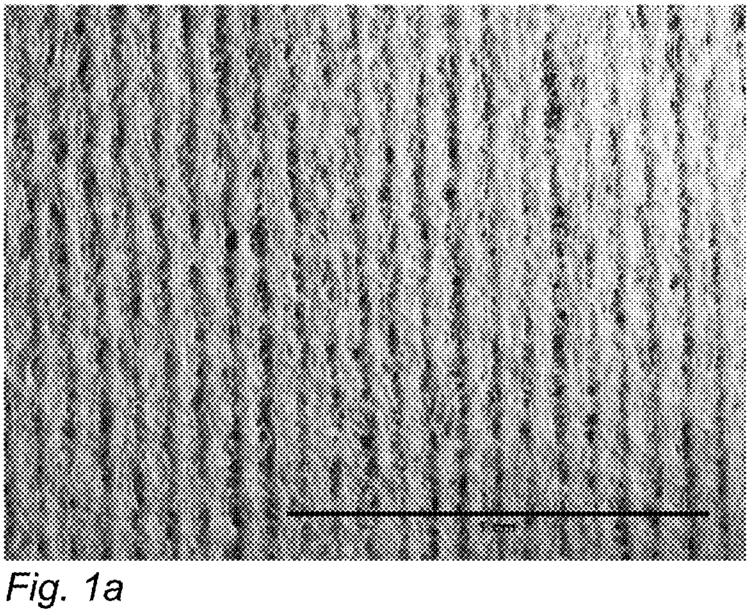
FIG. 1*a-b* are microscope photos of Sample A, made of an absorbent fibrous web as described herein.
Figure 1B:
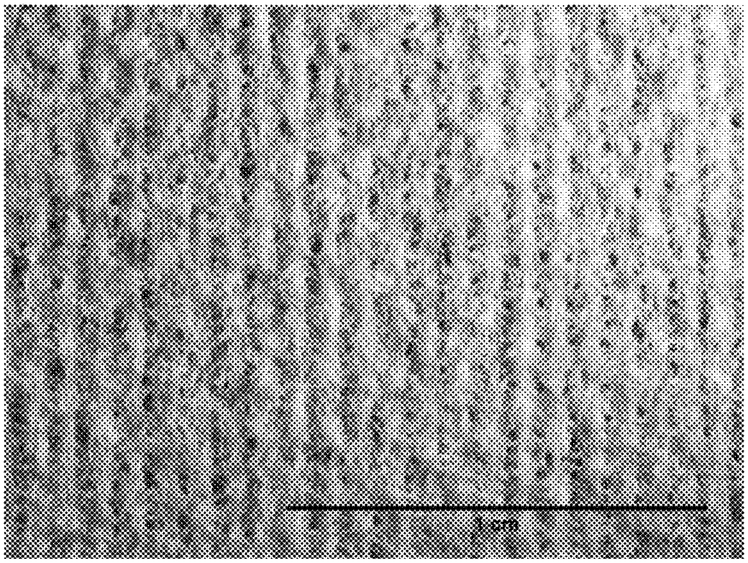

The following samples were compared to each other:

Sample A:

A foam-formed and hydroentangled absorbent fibrous web material as described herein. Grammage 45.5 gsm. The fibres were 15% viscose, commercial 1.7 dtex 10 mm Danufil, Kelheim, and 85% unrefined bleached softwood kraft pulp. The material has also been micro-embossed with a pattern having 80 dots/cm$^2$. Please see FIGS. 1*a* and 1*b*, wherein FIG. 1*a* shows the side facing the hydroentangling jets and FIG. 1*b* shows the side facing the hydroentangling fabric. Hydroentangling was made with 294 kWh/t at a machine speed of 10 m/min.

Figure 2A:
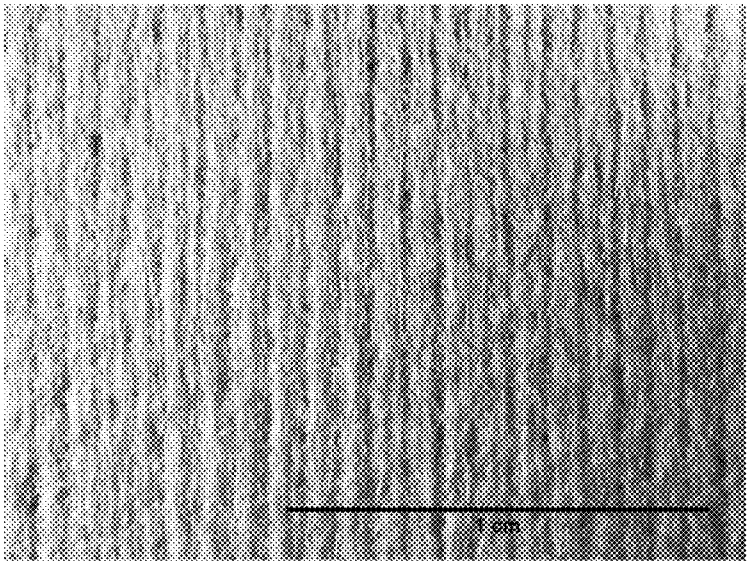
FIG. 2*a*-*b* are microscope photos of Sample B, made of an absorbent fibrous web as described herein.
Figure 2B:
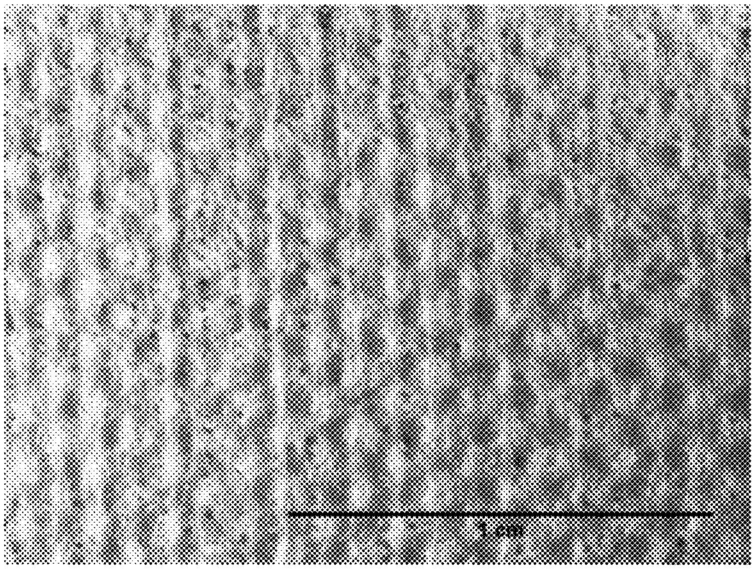

Sample B:

A foam-formed and hydroentangled absorbent fibrous web material as described herein. Grammage 58.8 gsm. The fibres were 17% viscose, commercial 0.9 dtex 8 mm Danufil, Kelheim, and 83% RaumaCell Biobright TCF from UPM Kymmene. The material has also been micro-embossed with a pattern having 80 dots/cm$^2$. Please see FIGS. 2*a* and 2*b*, wherein FIG. 2*a* shows the side facing the hydroentangling jets and FIG. 2*b* shows the side facing the hydroentangling fabric. Hydroentangling was made with 147 kWh/t at a machine speed of 139 m/min.

Figure 3A:
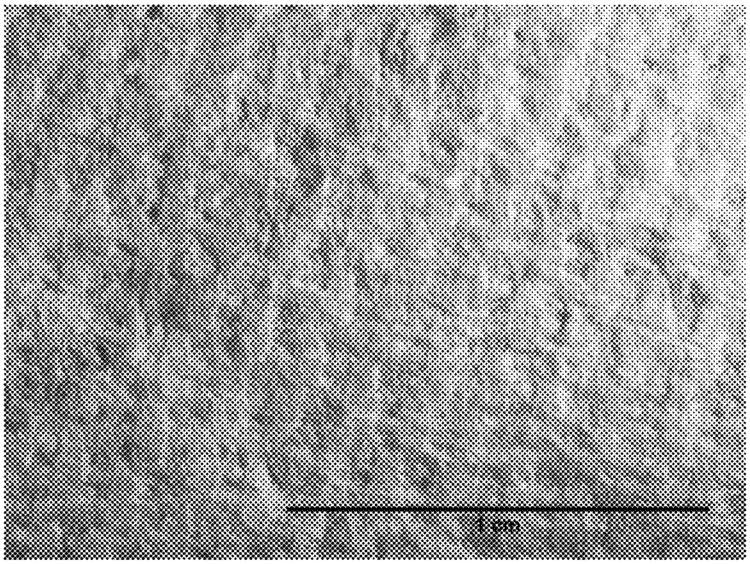
FIG. 3*a*-*b* are microscope photos of Sample C, a 2-ply tissue product according to prior art.
Figure 3B:
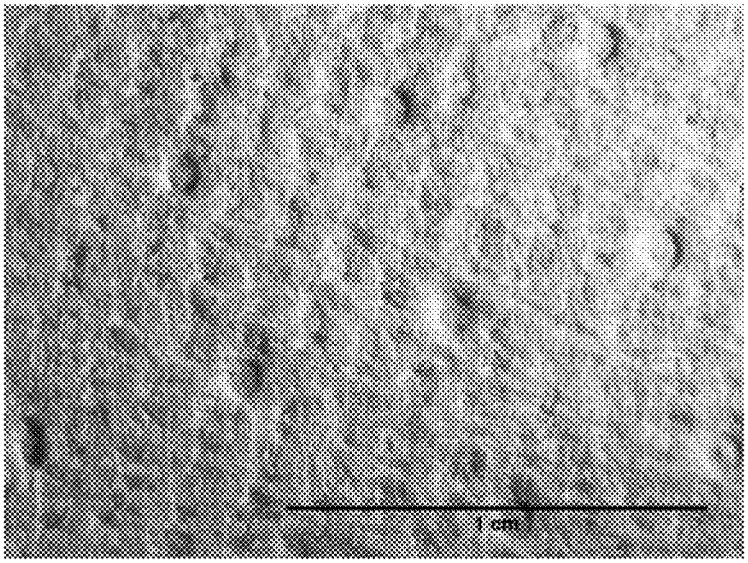

(having a pink décor) had a basis weight of 20.7±0.1 gsm and the second ply 20.8±0.2 gsm. Please see FIGS. 3*a* and 3*b*, wherein FIG. 3*a* shows the décor side and FIG. 3*b* shows the opposite side. Both plies are made of structured tissue paper and comprise a wet strength agent but no softener. The fibres are virgin pulp fibres. The term "structured tissue paper" as used herein denotes a tissue paper having a three-dimensional structure, such as tissue paper manufactured with TAD or ATMOS™ technology.

Figure 4A:
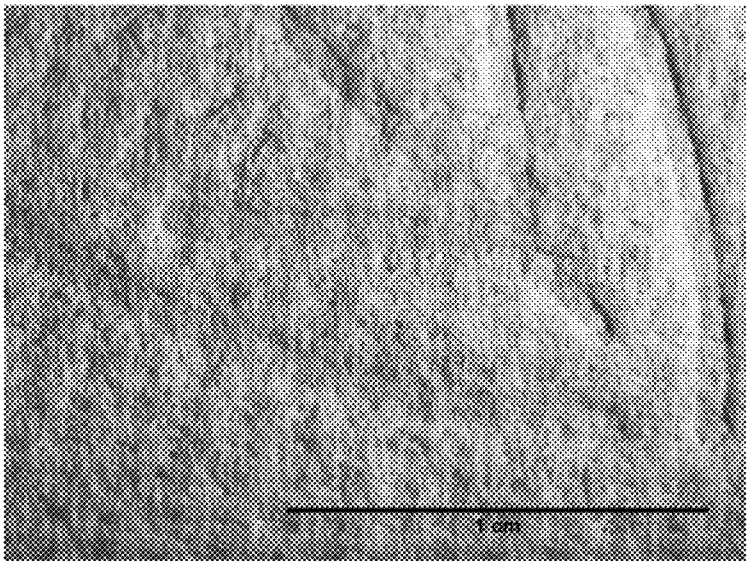
FIG. 4*a*-*b* are microscope photos of Sample D, another 2-ply tissue product according to prior art.
Figure 4B:
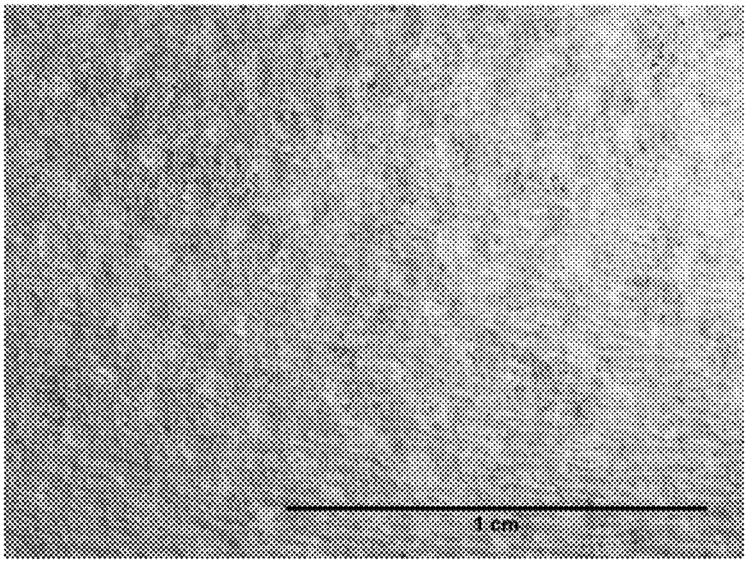

Sample D:

A hand towel being on the market: Tork Xpress® Soft Multi-fold Hand Towel Premium, art no 100288, the adhesive of the décor-embossing has a blue colour. One ply is a structured tissue paper 21.1±0.1 gsm and the other ply is a dry-crepe tissue paper 23.5±0.1 gsm. Please see FIGS. 4*a* and 4*b*, wherein FIG. 4*a* shows the decor-embossed side, i.e. the structured tissue paper side, and FIG. 4*b* shows the opposite side, i.e. the dry-crepe tissue paper side. Both plies comprise a wet strength agent but no softener. The fibres are virgin pulp fibres.

The photos shown in FIGS. 1*a*-4*b* have all been taken in a microscope using the same magnification, such that the image shown corresponds to a region of 17.5×13 millimetres in the sample.

Table 1 below describes some of the characterizing properties of Samples A-D, please see columns 3-6. The values after ±show the standard deviation.

In addition, comparisons have been made for some of the parameters to the intermediate web of Sample A, i.e. the absorbent fibrous web as is without any hydroentangling or micro-embossing, please see column 1 of Table 1 below.

Further, comparisons were made for some of the parameters to the absorbent fibrous web of Sample A, hydroentangled but without any micro-embossing, please see column 2 of the Table 1 below.

TABLE 1

| | Column | | | | | |
|---|---|---|---|---|---|---|
| | 1 | 2 | 3 | 4 | 5 | 6 |
| Name | A (raw) | A (raw + hydroent angled) | Sample A | Sample B | Sample C | Sample D |
| Photo | | | 1a-b | 2a-b | 3a-b | 4a-b |
| Grammage (g/m$^2$) | 48.7 ± 0.8 | 47.8 ± 0.7 | 45.5 ± 0.4 | 58.8 ± 1.1 | 41.6 ± 0.4 | 44.7 ± 0.2 |
| Bulk (cm$^3$/g) | 5.9 0.7 | 10.6 ± 0.1 | 10.4 ± 0.2 | 7.5 ± 0.1 | 9.8 ± 0.3 | 8.4 ± 0.3 |
| Air Permeability @200Pa 20cm$^2$ (mm/s) | 650 ± 10 | 2317 ± 31 | 1917 ± 42 | 1160 ± 42 | 520 ± 13 | 237 ± 4 |
| Wetting Time (s)—MMT | 2.6 ± 0.17 | 1.9 ± 0.13 | 1.9 ± 0.14 | 2.1 ± 0.16 | 2.5 ± 0.61 | 2.1 ± 0.14 |
| Spreading Speed (mm/s)—MMT | 5.3 ± 0.28 | 10.3 ± 0.53 | 10.7 ± 0.72 | 8.3 ± 0.33 | 7.7 ± 0.80 | 9.0 ± 0.58 |
| TS7 Softness—TSA | 22.9 ± 1.8 | 17.6 ± 1.4 | 13.7 ± 0.6 | 16.4 ± 2.0 | 25.5 ± 2.4 | 27.2 ± 4.1 |
| TS750 Roughness—TSA | 35.1 ± 7.4 | 19.9 ± 2.7 | 18.8 ± 3.4 | 39.2 ± 6.3 | 38.8 ± 5.2 | 42.6 ± 5.8 |
| Absorption Time (s)—AWR | | | 0.87 ± 0.12 | 0.45 ± 0.06 | 0.65 ± 0.12 | 1.08 ± 0.08 |
| Water Spreading Length MD (mm)—AWR | | | 87 ± 4.1 | 68 ± 7.7 | 59 ± 2.5 | 59 ± 4.8 |
| Rewet (g)—AWR | | | 0.31 ± 0.01 | 0.24 ± 0.01 | 0.34 ± 0.005 | 0.34 ± 0.01 |
| Panel: handled dry | | | 5.69 | 5.28 | 3.97 | 3.53 |
| Panel: hand wiping experience" | | | 5.03 | 5.61 | 4.36 | 3.89 |

Sample C:

A hand towel being on the market: Tork Xpress® Extra Soft Multifold Hand Towel Premium, art no 100297, a 2-ply tissue hand towel. For the tested samples, the first ply When comparing the two left-hand columns, it may be seen that the step of hydroentangling increased the Air Permeability about 3.6 times. The Bulk and the Spreading Speed were almost doubled. The hydroentangling also had a positive influence on the TS7 and TS750 values as measured with the TSA method described herein.

When looking at Samples A-D, it can be seen that there is a huge difference in Air Permeability when comparing Samples A and B, made of absorbent fibrous webs as disclosed herein, to Samples C and D, which are hand towels available on the market. The absorbent fibrous web as disclosed herein may have an Air Permeability of at least 800 mm/s, such as at least 1000 mm/s, at least 1500 mm/s, at least 1800 mm/s. Please note that all Air Permeability measurements have been made for samples like the photos in FIGS. 1*a*-4*b*. There are thus no deliberately made apertures in the tested materials. Please see also the method description above.

The hand feel of Samples A-D were tested by means of the TSA method described herein. As may be seen for both TS7 Softness and TS750 Roughness, Samples A and B have much lower values than Samples C and D, indicating a softer and more textile-like material. The absorbent fibrous web as disclosed herein may have a TS7 Softness value of less than 25, such as less than 20 or less than 18. The absorbent fibrous web as disclosed herein may have a TS750 Roughness value of less than 40, such as less than 30, less than 25, or less than 20.

The absorbent fibrous web as disclosed herein may have a Wetting Time, as measured with the MMT method described herein, taken as an average for both surfaces of the absorbent fibrous web, i.e. an average of the five samples mentioned above, and as an average of top and bottom, of less than 2.3 s, such as less than 2.2 s, less than 2.1 s, or less than 2.0 s. Also for this parameter, the hydroentangling influences the value as may be seen when comparing columns 1 and 2.

The absorbent fibrous web as disclosed herein may have a Spreading Speed, as measured with the MMT method described herein, taken as an average for both surfaces of the absorbent fibrous web and as an average of top and bottom, of over 6 mm/s, such as in the range of 6-18 mm/s, 8-16 mm/s or 10-15 mm/s. As may be seen when comparing columns 1 and 2, the hydroentangling has a huge influence on the Spreading Speed.

The parameters Absorption Time, Water Spreading Length MD and Rewet were tested with the AWR method as described above. Thereby Sample A and B were measured with the hydroentangled side upwards and Samples C and D were measured with the décor side upwards, meaning that the testing liquid was applied to this side. Please see also FIGS. 1*a*, 2*a*, 3*a* and 4*a*. Sample A has a significantly shorter absorption time than Sample D. Further, Samples A and B have a higher Water Spreading Length MD than Samples C and D. All samples spread the testing liquid all the way to the side edge in CD, and would have spread further if possible. Hence, the CD values are not included in Table 1.

The absorbent fibrous web as disclosed herein may have an Absorption Time of less than 1.0 s, such as less than 0.9 s, as measured with the AWR method described herein, please see method description above.

The absorbent fibrous web as disclosed herein may have a Water Spreading Length in the machine direction, MD, of the absorbent fibrous web of at least 60 mm, such as at least 70 mm or at least 80 mm. Please see also the method description of the AWR method above.

Samples A-D were also tested in a panel test involving 36 persons in a dry state and used for hand wiping. Please, see the method description above and the data of the two lowermost rows of Table 1.

As may be seen, Samples A and B scored significantly better than Samples C and D when handled dry. Further, Sample C scored better than Sample D. These results correlate well with the results of the TSA-method.

Samples A and B also scored significantly better than Samples C and D when used for hand wiping. Sample B scored better than Sample A, which is believed to be an effect of the higher grammage. Further, Sample C scored better than Sample D.

Table 2 illustrates, with another example, the huge influence the hydro-entangling step has on the air permeability and the bulk. Both materials of Table 2 were foam-formed of the same fibre composition, 15% lyocell, 1.4 dtex 10 mm from Lenzing and 85% International Paper Supersoft pulp. The material to the left was manufactured at a machine speed of 94 m/min, but without any hydroentangling. The material to the right was manufactured at a machine speed of 91 m/min with hydroentangling energy of 232 kWh/t. None of the materials were micro-embossed.

TABLE 2

| | Material without hydroentangling | Material with hydroentangling |
|---|---|---|
| Grammage (g/m$^2$) | 47.0 ± 0.5 | 43.8 ± 1.2 |
| Bulk (cm$^3$/g) | 7.8 ± 0.7 | 14.3 ± 0.4 |
| Air permeability @ 200Pa 20 cm$^2$ (mm/s) | 830 ± 64 | 3350 ± 103 |

As may be seen from the data of Table 2, the bulk almost doubled for the hydro-entangled material, while air permeability increased 4 times. In general terms, the step of hydroentangling may at least double, such as triple or quadruple, the air permeability.

Further modifications of the absorbent fibrous web within the scope of the appended claims are feasible. As such, the present disclosure should not be considered as limited by the embodiments and figures described herein. Rather, the full scope of the disclosure should be determined by the appended claims, with reference to the description and figures.

The invention claimed is:

1. An absorbent fibrous web, comprising a foam-formed hydro-entangled fibrous web, the fibres of the absorbent fibrous web being constituted by only cellulosic fibres comprising cellulosic staple fibres and cellulose pulp fibres, wherein the cellulosic fibres located in a first surface layer have a sufficiently similar fibre composition and a sufficiently similar orientation of fibres as the cellulosic fibres located at a second surface layer being opposite to the first surface layer in order to avoid two-sidedness, wherein the fibres extend at least partly in the Z-direction of the web, wherein the Z-direction is the thickness direction of the web, and wherein the cellulosic staple fibres make up in the range of 2-25% of a total weight of the cellulosic fibres, and wherein the web has a Spreading Speed, as measured with an MMT method described herein, taken as an average for both surface layers of the absorbent fibrous web and as an average of top and bottom, of over 6 mm/s.

2. The absorbent fibrous web according to claim 1, wherein the cellulosic staple fibres are regenerated cellulosic fibres.

3. The absorbent fibrous web according to claim 1, wherein the cellulosic staple fibres and the cellulose pulp fibres are mixed with each other.

4. The absorbent fibrous web according to claim 1, wherein the cellulosic staple fibres have a length in the range of 2-25 mm.

5. The absorbent fibrous web according to claim 1, wherein the cellulosic staple fibres have a linear density within the range of 0.3-3 dtex.

6. The absorbent fibrous web according to claim 1, wherein the cellulosic staple fibres make up in the range of 10-17% of a total weight of the cellulosic fibres.

7. The absorbent fibrous web according to claim 1, wherein the cellulose pulp fibres make up in the range of 50-98% of a total weight of the cellulosic fibres.

8. The absorbent fibrous web according to claim 1, having a basis weight in the range of 10-250 gsm.

9. The absorbent fibrous web according to claim 1, wherein the absorbent fibrous web is micro-embossed.

10. The absorbent fibrous web according to claim 1, having a TS7 Softness value of less than 25 as measured with a TSA method described herein.

11. The absorbent fibrous web according to claim 1, having a Wetting Time, as measured with an MMT method described herein, taken as an average for both surface layers of the absorbent fibrous web and as an average of top and bottom, of less than 2.3 s.

12. The absorbent fibrous web according to claim 1, having an Air Permeability of at least 800 mm/s as measured with an Air Permeability method described herein.

13. The absorbent fibrous web according to claim 1, wherein during formation of the web, the fibres are fed between two permeable fabrics dewatered through each of the two permeable fabrics so that the orientation of the fibres in the web are symmetrical in a direction perpendicular to the two surface layers.

14. A method of wiping with the absorbent fibrous web according to claim 1, wherein the absorbent fibrous web is one of a hand wiping material, a hygiene tissue and a layer in an absorbent article for absorption of a body fluid.

15. A method of manufacturing an absorbent fibrous web according to claim 1, wherein the method comprises:
- foam-forming a mixture of cellulosic fibres, the cellulosic fibres comprising cellulosic staple fibres and cellulose pulp fibres,
- two-sided dewatering of the mixture to form an intermediate web, and
- hydro-entangling the intermediate web.

16. The method according to claim 15 further comprising micro-embossing on at least one surface of the absorbent fibrous web.

17. An absorbent fibrous web, comprising a foam-formed hydro-entangled fibrous web having a first surface layer and a second surface layer, the fibres of the absorbent fibrous web being constituted only by cellulosic fibres comprising cellulosic staple fibres and cellulose pulp fibres,
- wherein during formation of the web, the fibres are fed between two permeable fabrics dewatered through each of the two permeable fabrics so that the orientation of the fibres in the web are symmetrical in a direction perpendicular to the two surface layers,
- wherein the fibres extend at least partly in the Z-direction of the web, wherein the Z-direction is the thickness direction of the web, and wherein the cellulosic staple fibres make up in the range of 2-25% of a total weight of the cellulosic fibres, and
- wherein the web has a Wetting Time, as measured with an MMT method described herein, taken as an average for both surface layers of the absorbent fibrous web and as an average of top and bottom, of less than 2.3 s.

18. The absorbent fibrous web according to claim 17, having a TS750 Roughness value of less than 30 as measured with a TSA method described herein.

19. The absorbent fibrous web according to claim 1, having a Spreading Speed, as measured with an MMT method described herein, taken as an average for both surface layers of the absorbent fibrous web and as an average of top and bottom, of over 6 mm/s.

20. An absorbent fibrous web, comprising a foam-formed hydro-entangled fibrous web, the fibres of the absorbent fibrous web being constituted by only cellulosic fibres comprising cellulosic staple fibres and cellulose pulp fibres,
- wherein the cellulosic fibres located in a first surface layer have a sufficiently similar fibre composition and a sufficiently similar orientation of fibres as the cellulosic fibres located at a second surface layer being opposite to the first surface layer in order to avoid two-sidedness,
- wherein the fibres extend at least partly in the Z-direction of the web, wherein the Z-direction is the thickness direction of the web, and wherein the cellulosic staple fibres make up in the range of 2-25% of a total weight of the cellulosic fibres, and
- wherein the web has an Absorption Time of less than 1.0 s as measured with an AWR method described herein.

21. An absorbent fibrous web, comprising a foam-formed hydro-entangled fibrous web, the fibres of the absorbent fibrous web being constituted by only cellulosic fibres comprising cellulosic staple fibres and cellulose pulp fibres,
- wherein the cellulosic fibres located in a first surface layer have a sufficiently similar fibre composition and a sufficiently similar orientation of fibres as the cellulosic fibres located at a second surface layer being opposite to the first surface layer in order to avoid two-sidedness,
- wherein the fibres extend at least partly in the Z-direction of the web, wherein the Z-direction is the thickness direction of the web, and wherein the cellulosic staple fibres make up in the range of 2-25% of a total weight of the cellulosic fibres, and
- wherein the web has a Water Spreading Length in a machine direction of the absorbent fibrous web of at least 60 mm as measured with an AWR method described herein.

* * * * *